United States Patent [19]
Schermer et al.

[11] Patent Number: 6,075,613
[45] Date of Patent: Jun. 13, 2000

[54] OPTICAL SCANNER CALIBRATION DEVICE

[75] Inventors: Mack Schermer, Belmont; Hans Bengtsson, Sudbury; Markus Weber, Arlington, all of Mass.

[73] Assignee: General Scanning, Inc., Watertown, Mass.

[21] Appl. No.: 09/258,872

[22] Filed: Feb. 26, 1999

[51] Int. Cl.$^7$ ..................................... G01N 21/55
[52] U.S. Cl. ........................ 356/446; 388/213; 388/445
[58] Field of Search .................................. 356/388, 213, 356/445, 446

[56] References Cited

U.S. PATENT DOCUMENTS

| | | |
|---|---|---|
| 4,681,444 | 7/1987 | Ferber et al. . |
| 4,868,126 | 9/1989 | Schwartz . |
| 4,918,004 | 4/1990 | Schwartz . |
| 5,424,537 | 6/1995 | Lehman et al. ........................ 250/235 |
| 5,515,161 | 5/1996 | Blumenfeld . |
| 5,672,880 | 9/1997 | Kain . |
| 5,689,110 | 11/1997 | Dietz et al. . |
| 5,719,391 | 2/1998 | Kain . |
| 5,838,435 | 11/1998 | Sandison . |

*Primary Examiner*—Frank G. Font
*Assistant Examiner*—Reginald A. Ratliff
*Attorney, Agent, or Firm*—Cesari and McKenna, LLP

[57] ABSTRACT

An optical scanning system includes a power meter that during calibration operations is illuminated by an attenuated excitation beam. The power meter measures optical power in the attenuated excitation beam at various index settings of a variable optical attenuator, and the system constructs a lookup table that relates incident excitation beam power to the index settings of the attenuator. The system then uses the table to select the appropriate setting for the attenuator in order to deliver to the sample an excitation beam of a specified optical power. The system calibrates the gain of a detector by redirecting, or reflecting, the excitation beam of known intensity to the detector. A photometric device in the detector produces a signal that is proportional to the intensity of the beam at various gain settings. The system then produces a lookup table that relates the gain settings to the actual gain of the detector, that is, to the ratio of the known incident power to the detector readings. The system thereafter uses the table to select the appropriate gain setting for data collection and/or to normalize the data. A beam splitter included in the system preferably discriminates between the light is passes and the light it redirects based on the spatial properties of the light. During calibration operations the excitation beam is reflected to the detector as wide diameter beams, which are passed through the beam splitter. During sample measurement operations the excitation beam is reflected by the sample as a narrow-diameter beam, which the beam splitter directs away from the detector.

29 Claims, 3 Drawing Sheets

OPTICAL SCANNER CALIBRATION DEVICE

FIELD OF INVENTION

The invention relates generally to optical scanning systems, and more particularly, to mechanisms for calibrating the scanning systems.

BACKGROUND OF THE INVENTION

Optical scanning systems essentially direct light produced by a resident light source to a sample and measure the light emitted or reflected by the sample. We discuss scanners below in the context of scanning laser microscopes that are used in fluorescent imaging. The inventive mechanism is not, however, limited to use as part of a scanning laser microscope or as part of a fluorescent imaging system.

A fluorescent imaging system examines fluorescence from chemically-tagged biological samples such as cells, proteins, genes and DNA sequences. The samples may be microarrays, which can include thousands of experiments on a single glass microscope slide. Each experiment consists of a spot of, for example, "target" DNA that is chemically bound to a surface of the glass slide. "Probe" DNA, or alternatively RNA, that has been labeled with a fluorophor is introduced to the surface of the slide and is allowed to hybridize with the target DNA. The sample is then optically scanned, using light of a desired wavelength, such that the fluorophor in the respective experiments emits light.

For a given sample, each experiment emits an amount of light that corresponds to the associated fluor density. The fluor density of an experiment depends on the similarity of the particular target DNA and the probe DNA, since complementary molecules have a greater probability of binding than unrelated molecules. A detector measures the intensity of the light emitted by each experiment included in the sample, and the system can then determine the relative degrees of similarity between the target DNA and the probe DNA.

The measurements associated with the sample depend not only on the fluor densities of the experiments but also on the sensitivity of the system. The system sensitivity depends, in turn, on the power of the incident excitation beam and the gain of the detector. The fluorescent imaging systems have relatively large adjustable ranges of sensitivity, to accommodate the extensive ranges of fluor densities. For example, it is common for the systems to have a dynamic range of four orders of magnitude that is adjustable over another four orders of magnitude. The sensitivity is set by adjusting the power of the incident excitation beam or the gain of the detector, or both.

It is difficult to maintain repeatability with systems having such large ranges of adjustability. Accordingly, for applications in which data are compared from one sample measurement to the next or from one system to the next, the accuracy of the sensitivity setting of the system and the overall calibration of the system are important. Changes in the incident power or the detector gain from what is expected at a given sensitivity setting adversely affect normalization of the data, unless the changes can be quantified.

The system controls the power of the incident excitation beam, which is typically produced by a laser, by including a variable attenuator in the beam path. The attenuator is characterized by an index-to-attenuation transfer curve. It is not uncommon, however, for there to be a relatively large discrepancy between the percentage of attenuation at the respective index settings and the transfer curve. Accordingly, there is often a discrepancy in the expected power of the incident excitation beam relative to the setting of the attenuator. Further, the operating characteristics of the laser may vary over time, such that there is a reduction of the nominal power of the excitation beam before attenuation. It is thus desirable to accurately and periodically characterize, or calibrate, the power level associated with each of the settings of the variable attenuator.

The gain of the detector depends in large part on the gain of the included photometric device. Generally, the device is a photo-multiplier tube, or PMT, which has a high sensitivity and adjustable gain. The detector gain is set by adjusting a DC voltage that is the reference for the PMT power supply. The transfer function of the reference voltage-to-PMT gain is grossly non-linear, however, and the operations of the individual PMTs typically vary from the transfer curve. Further, the operations of the PMTs vary with different wavelengths, and thus, vary between channels on a multiple-channel system. Accordingly, the PMT index settings are only rough estimates of the PMT gain. It is thus desirable to accurately characterize or calibrate the operations of the detector at the various PMT index settings.

Certain known prior systems calibrate system sensitivity by including in a sample or in the field of view of the system one or more reference spots with known fluorescence. These systems measure the fluorescent light emitted by the reference spots as well as the light emitted by the experiments, in the same measurement operation, and use the data associated with the reference spots to quantify the system sensitivity.

The reference spots may be made with fluorescent dyes or solid-state fluorescence. The spots made with fluorescent dyes are vulnerable to "photo-bleaching," and thus, the systems that use these spots may make inaccurate calibration measurements based on damaged spots, or may be unable to make calibration measurements for a given sample. The emission characteristics of the reference spots made of solid state fluorescent material vary with changes in the ambient environment, such as changes in temperature. Accordingly, the systems that use them must compensate for the environmental changes, which adds complexity to the system.

SUMMARY OF THE INVENTION

An optical scanning system uses a power meter to construct a lookup table that relates incident excitation beam power to the settings of a variable optical attenuator. The power meter, which is in the path of the incident excitation beam, is illuminated by the beam when the sample is not in place. The meter includes a silicon photodiode that produces a signal which is proportional to the intensity of the incident light. An A/D converter then produces a digital value that corresponds to the signal. The system varies the settings of the optical attenuator and produces the lookup table based on the associated digital values. The system then uses the table to select the appropriate setting for the attenuator in order to deliver to the sample an excitation beam of a specified optical power.

The optical scanning system calibrates the gain of a detector by directing a beam of known intensity to the detector. The photometric device in the detector produces a signal that is proportional to the intensity of the beam and an A/D converter produces a digital value that corresponds to the signal. The system varies the gain of the photometric device and produces the associated digital values at the various gain settings. It then produces a lookup table that relates the gain settings to the actual gain of the detector, that is, to the ratio of the known incident power to the digital readings. The system thereafter uses the table to select the appropriate gain setting for data collection and/or to normalize the data.

More specifically, the system includes in the incoming excitation beam path the variable optical attenuator, an objective lens that focuses the attenuated beam to the size of a pixel, and a beam splitter that directs the incoming excitation beam through the lens in the direction of the sample. The power meter sits below the sample, with the active area of the photodiode in line with the path of the focused beam. During calibration, the sample is not present and the focused incident excitation beam hits the active area of the photodiode. As discussed, the power meter produces the digital values that represent the incident optical power at the various attenuator settings.

The beam splitter preferably discriminates between the fluorescent light emitted by the sample and the laser light reflected by the sample based on the spatial properties of the light. The beam splitter, for example, includes in the path of the incoming excitation beam a mirror that redirects the incoming beam toward the sample. When the sample is in place, the surface of the sample partially reflects the incident excitation beam as a narrow-diameter beam and the fluorophors in the sample emit light in a spherical pattern. The reflected excitation light travels back from the sample along the same path as the incoming beam and is redirected to the light source by the mirror. In contrast, the emitted fluorescent light, which consists of relatively wide diameter beams, travels in whole or in part past the mirror, and thus, toward the detector.

For the calibration of the detector gain, the system uses a diffuse reflector in place of the sample. The diffuse reflector reflects the focused excitation beam in a diffused pattern, such that a portion of the reflected light passes through the beam splitter. A neutral density filter with known properties is positioned between the beam splitter and the detector, to attenuate the reflected light by a predetermined percentage and reduce the intensity of the light to within the linear operating range of the detector. The detector then produces the various digital values associated with the various PMT gain settings.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
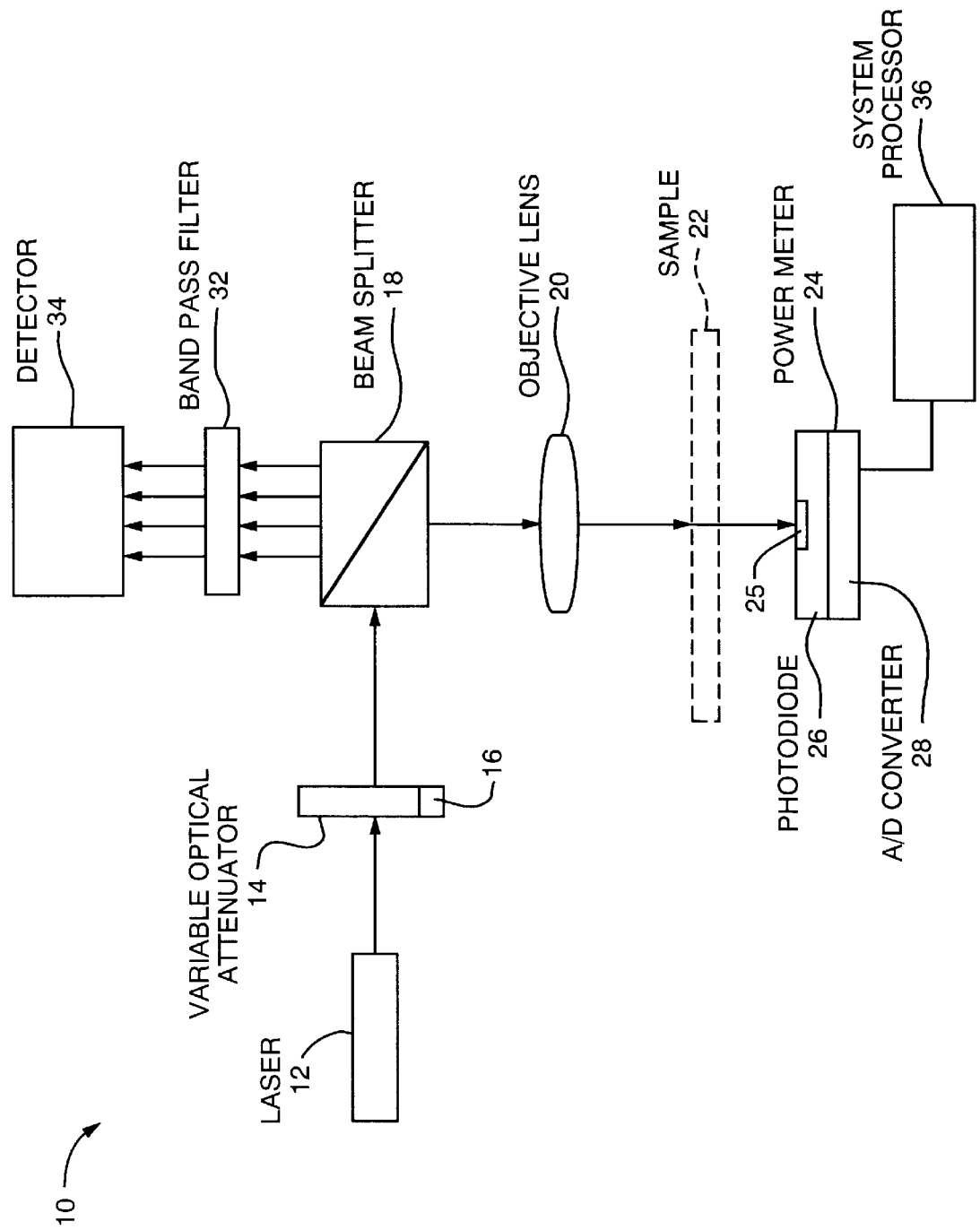
FIG. 1 is a functional block diagram of a system for calibrating the power in the excitation beam.

Referring to FIG. 1, a fluorescent imaging system 10 constructed in accordance with the invention includes a laser 12 that directs a collimated excitation beam to a variable optical attenuator 14. The variable optical attenuator 14 in the system 10 is a continuous wedge neutral-density filter that is mounted on a stepper motor 16, such that at any give time each index setting of the stepper motor 16 is associated with a unique attenuation factor. The attenuated beam passes from the attenuator 14 to a beam splitter 18 that redirects the incoming beam in the direction of a sample 22, which is depicted by dotted lines in the drawing. An objective lens 20 focuses the beam to a pixel-sized diameter, and during measurement operations the sample 22 is moved such that the focused beam successively illuminates each pixel in a scanning range.

Figure 2:
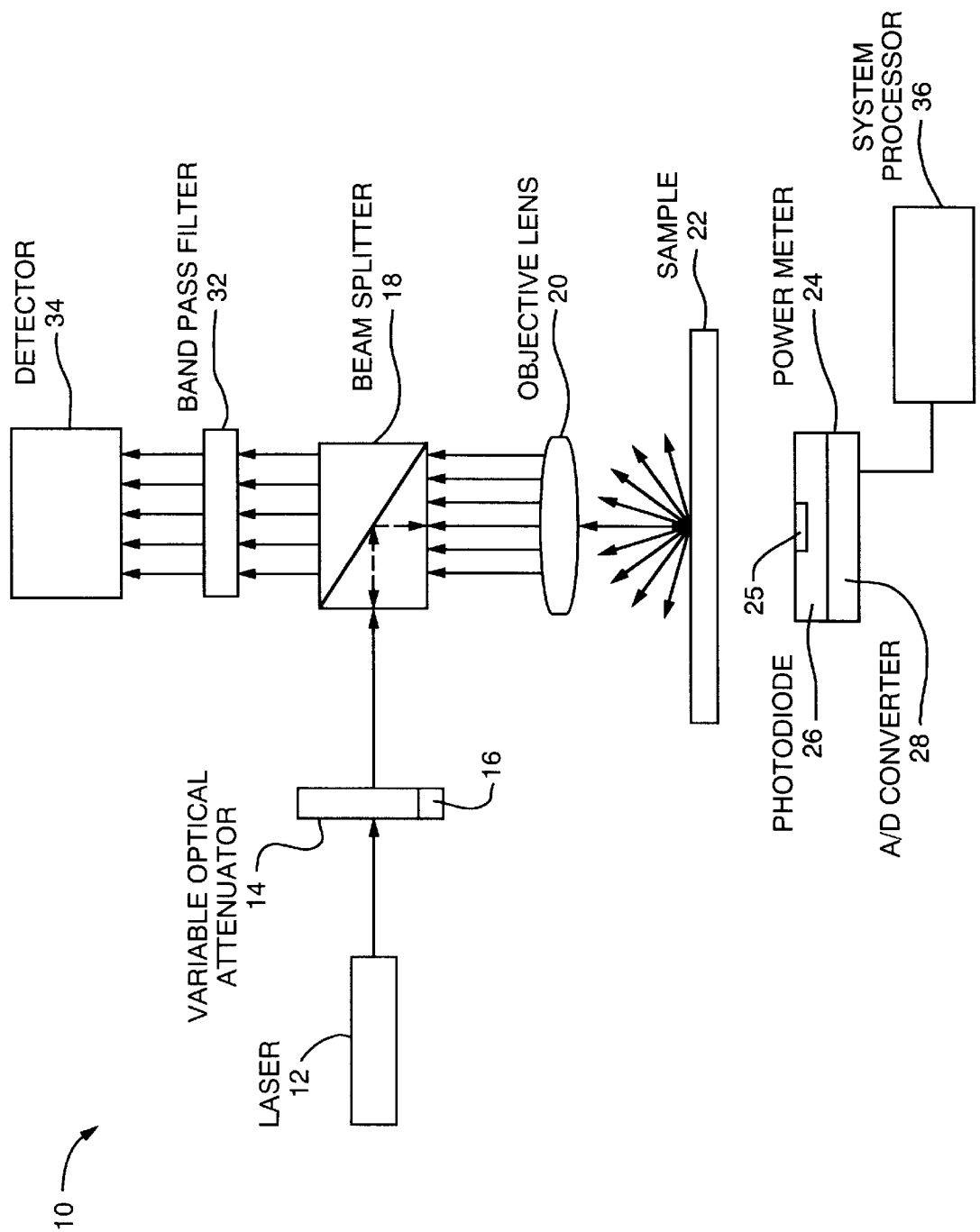
FIG. 2 is a functional block diagram of the system of FIG. 1 with a sample in place.

Referring now to FIG. 2, when the sample 22 is in place, the fluorophors in the experiments included therein emit fluorescent light in a spherical pattern, and a surface of the sample reflects and scatters some of the light from the focused incident excitation beam. The lens 20 collects portions of the fluorescent light and the reflected and scattered light, and directs the collected light to the beam splitter 18. The beam splitter 18 passes the collected emitted light in the direction of the detector 34 and, as depicted by the dotted lines, redirects or rejects the reflected and scattered light. A bandpass filter 32, which is positioned between the beam splitter 18 and the detector 34, passes the emitted light on to the detector and rejects any residual excitation light that passes through the beam splitter 18. The beam splitter is discussed in more detail below with reference to FIG. 3.

The detector 34 produces a digital value that corresponds to the intensity of the light emitted by a given experiment. A system processor 36 then maps the digital value to a degree of similarity between the associated target DNA and the probe DNA. The operations of the detector are also discussed in more detail below with reference to FIG. 3.

Referring again to FIG. 1, the sample 22 is not in place for calibration. The excitation beam instead illuminates a power meter 24 that is positioned in the beam path. The power meter 24 consists essentially of a photodiode 26 and an A/D converter 28. The excitation beam, expanding past its focus, strikes an active area 25 of the photodiode 26. In response, the photodiode produces a current that is proportional to the incident optical power. The A/D converter 28 converts the current to a corresponding digital value and provides the digital value to the system processor 36. The photodiode 26 may be positioned on a substrate scanning stage 32 (FIG. 2) that holds the sample during measurement operations, such that the active area 25 is covered by the sample when the sample is in place. Alternatively, the photodiode 26 may be located at one end of the stage and outside the normal measurement range. The stage is then moved beyond the measurement range during calibration, to bring the photodiode into the path of the excitation beam.

The system measures the optical power in the incident excitation beam at each of the settings of the variable optical attenuator 14. Accordingly, the motor 16 steps through its various index settings and the power meter 24 produces associated digital values. Based on the digital values, the system processor 36 produces a look-up table that relates incident optical power to the attenuator settings. A user can then specify the desired optical power to be delivered to a sample, and the system operates the variable optical attenuator 14 at the appropriate setting. The calibration of the incident optical power in this manner allows a user to set the power level to just below the photo-bleaching level, and thus, maximize data collection without damaging the sample.

In the system 10, the photodiode 26 is a silicon photodiode, which has a linear power-to-current transfer curve over approximately nine decades of dynamic range and over applicable wavelengths. Further, the silicon photodiode is stable over both time and temperature. Accordingly, the operations of the silicon photodiode are repeatable in the same device and between individual devices.

The calibration of the incident power at the various attenuator settings is preferably performed periodically, to compensate for changes in the operations of the attenuator 14 and/or the laser 12 over time. For example, gas lasers typically lose power over time, and thus, the power in the incident excitation beam is reduced at each of the attenuator settings. Based on the reduction in nominal power, the system may also predict when the laser will fail. The laser can then be replaced, to avoid failure during measurement operations.

The incident beam calibration operations discussed above are preferably used in a system in which the power in the incident beam remains constant over the scanned field, such as a system with stationary optics and a moving sample. In contrast, the power in a scanned beam varies over the scanned field as the angle of incidence varies and thus, a power reading at one point in the scanned field provides less accurate calibration information. Alternatively, the power meter may use a plurality of silicon diodes 26 spaced over the scanning field, to calibrate the incident optical power at various associated angles of incidence.

The system 10 may have multiple channels, and thus, include a plurality of lasers 12 that produce light of different wavelengths. The system then calibrates the power versus attenuator setting separately for each channel, since the attenuation and photodiode response may differ for different wavelengths.

Figure 3:
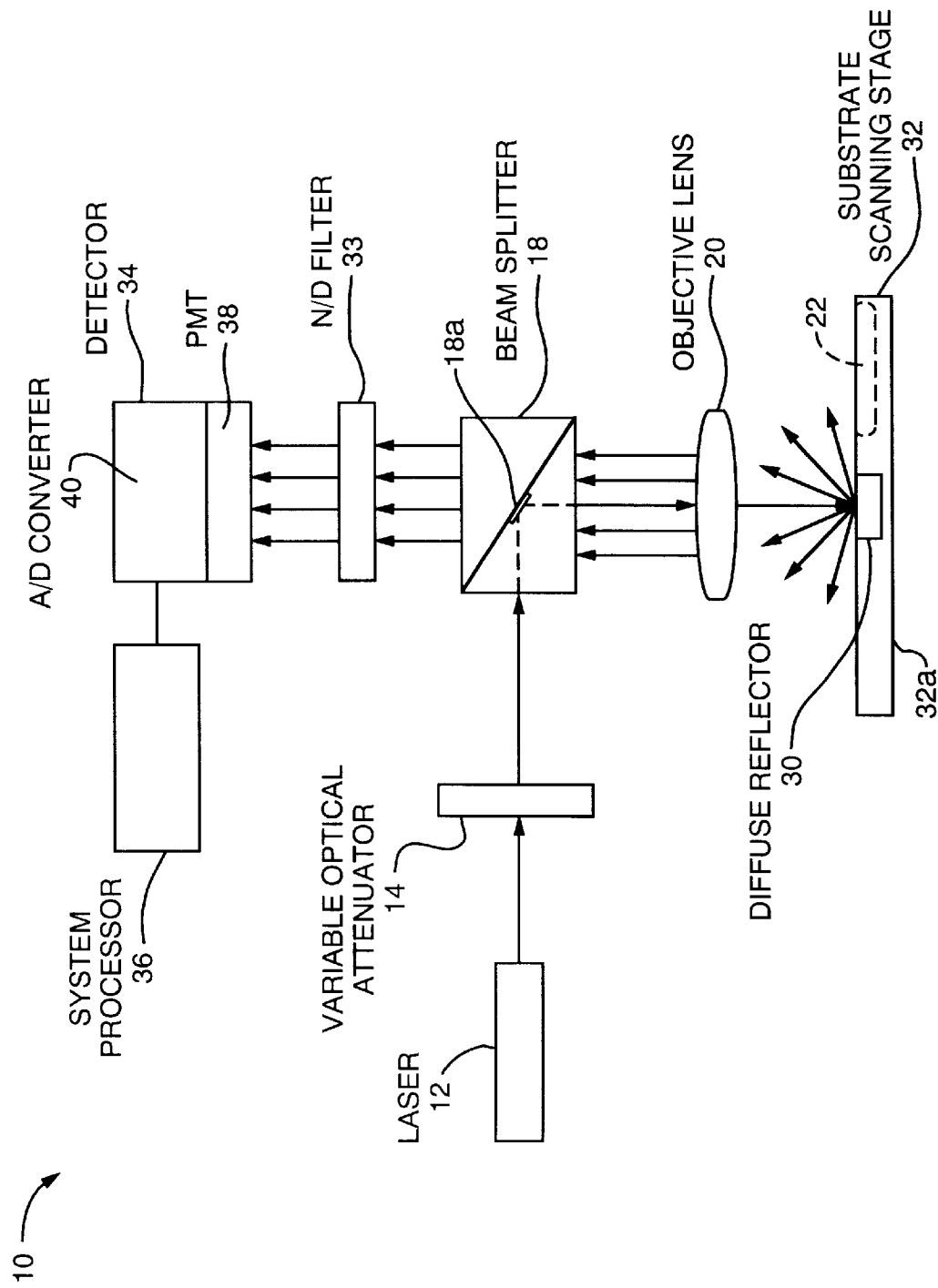
FIG. 3 is a functional block diagram of the system of FIG. 1 modified for calibration of detector gain.

Referring now to FIG. 3, the system calibrates the detector gain by directing reflected beams with known intensities to the detector 34. The detector includes a PMT 38 that produces signals which are proportional to the intensities of the beams and an A/D converter 40 that produces digital values that correspond to the signals. During calibration operations, the PMT is operated at its various gain settings and the system processor 36 produces a look-up table that relates the gain setting of the PMT to the gain of the detector, that is, to the ratio of the power of the incident beam to the digital values.

To direct the beams to the detector 34, a diffuse reflector 30 with known properties is placed in the path of the focused incident excitation beam. The reflector 30 reflects the focused beam in a diffused pattern. The lens 20 collects a portion of the reflected beam and the beam splitter 18 passes all or a portion of the reflected light. A neutral density filter 33, which takes the place of the bandpass filter 32 (FIG. 1), attenuates the reflected light by a predetermined percentage before passing the light to the detector 34. The intensity of the reflected light, which is many times that of the emitted light, is thus reduced to within the linear operating range of the detector. The neutral density filter 33 has precisely controlled transmission properties, and thus, the intensity of the beam that reaches the detector is known.

The diffuse reflector 30 may, for example, reside on one end 32a of a substrate scanning stage 32 that holds the sample during measurement operations. The stage 32 is driven past the end of the normal measurement range during calibration operations, to position the reflector 30 in the path of the focused beam. Alternatively, the diffuse reflector 30 may be mounted on a sample substrate that is scanned for calibration.

In the system depicted in FIG. 3, the beam splitter 18 preferably discriminates between the reflected excitation beam and the emitted fluorescence based on the spatial properties of the light, rather than on the different wavelengths of the light. As shown in the drawing, the beam splitter 18 includes a small-diameter mirror 18a that is positioned in the path of the incoming excitation beam. The mirror directs the incoming beam through the focusing lens 20 and in the direction of the sample 22. When the sample is in place, the sample emits fluorescent light in a spherical pattern and reflects a portion of the focused beam as a narrow-diameter beam. The reflected excitation beam is directed back along the path of the incoming excitation beam, and the mirror 18a is thus in the return path. The mirror 18a re-directs the reflected beam toward the laser 12, while most of the collected emitted light, which consists of wider-diameter beams, passes by the mirror 18a. During calibration operations, the incident excitation beam is reflected in a diffused pattern, and thus, as wide-diameter beams that pass in large part by the mirror 18a.

Alternatively, the beam splitter may include a wide diameter mirror (not shown) with a hole in it. This mirror reflects the emitted fluorescence toward the detector and allows the focus excitation beam and its reflection to pass through the hole.

The geometric beam splitter works best in systems that have narrower diameter incident excitation beams and wider diameter emitted beams, such as a system with stationary optics and a moving sample or a system with a scanned objective lens that collects a relatively large fraction of the emitted light.

In order to calibrate the detector over a broader range, several different neutral density filters may be used to attenuate the reflected light by various, controlled percentages. The filter 33 may then be included in a filter wheel (not shown) that the system rotates during the calibration operations, to bring the various neutral density filters into the path of the reflected beam at appropriate times. The filter wheel may also include the bandpass filter 32 (FIG. 1), which is rotated into position during measurement operations.

During calibration operations, the system varies the gain of the PMT 38 and the system processor 36 uses the associated detector readings to produce a look-up table that relates PMT gain settings to detector gain. The calibration operations are preferably performed periodically, so that the system can compensate for changes in the PMT operations over time. In multiple-channel systems, the gain of the PMT is separately calibrated for each of the channels, that is, for each of the different wavelengths.

The emitted light produced in response to the incident excitation beam during measurement operations is separated from the wavelength of the excitation beam by only 20 to 40 nm. Accordingly, the operations of the PMT during calibration with the reflected excitation beam are sufficiently close to those during the measurement operations that the lookup table provides accurate calibration information. Further, using the reflected laser light allows for calibration over the various wavelengths associated with multiple-channel systems, since the power of the incident beam in each channel is known through calibration. In contrast, systems that use fluorescent light for calibration must contend with variations in the chromatic distribution of power in the fluorescent light over time and with changes in environmental conditions.

The system may instead use a beam splitter that discriminates between the reflected light and the emitted light based on their wavelengths, if the percentage of light that the beam splitter passes is known for each rejected wavelength of interest. The attenuation of the reflected signal that reaches the detector would then be based on the known attenuation through both the beam splitter 18 and the neutral density filter 33. Typically, however, beam splitters include optics that are manufactured to pass no more than a predetermined maximum percentage of the light of a given rejected wavelength. The percentage of the light of the given wavelength that actually passes through the optics is not otherwise controlled, and the beam splitter then becomes a variable in the calibration operations.

The calibration mechanisms discussed above may also be used to normalize the sensitivity of instruments produced by a given manufacturer. This would allow experiments performed by different instruments to be compared, whether the instruments are at the same site or at different sites and/or are used by the same or different sets of researchers. To achieve normalized calibration, the manufacturer selects performance limits. For example, the manufacturer specifies a working range for its instruments that is less than the maximum operating range, and constrains the adjustments that the user may make to within the selected working range. The manufacturer then sets the power and gain settings identically within the selected range for every instrument. Thereafter, the user maintains the accuracy of the settings over the life of the instruments using the calibration operations discussed above, and the data taken by each of these instruments remains consistent.

The system of FIGS. 1 and 2 provides a user with reliable and easily performed calibration operations. To calibrate the incident optical power by attenuator gain settings, the user operates the system without the sample, and the resident power meter 24 produces the appropriate readings. The system then calibrates the detector gain based on the calibrated optical power, by moving the sample stage 32 beyond the measurement range, rotating the filter wheel to bring the appropriate attenuating filter or filters 33 into the path of the reflected beam, as necessary, and taking readings from the detector 24. There are thus no special calibration subsystems that must be put in place by the user, and/or special reference spots that must be included in the samples.

The foregoing description has been limited to a specific embodiment of this invention. It will be apparent, however, that variations and modifications may be made to the invention, such as the use of different types of variable optical attenuators, beam splitters and/or reflectors, or incorporating in the system the mechanism to calibrate one of the detector gain or the attenuator gain, with the attainment of some or all of its advantages. Therefore, it is the object of the appended claims to cover all such variations and modifications as come within the true spirit and scope of the invention.

What is claimed is:

1. A system for calibrating the sensitivity of an optical scanner, the system including:
   A. optical means for producing an incoming excitation beam of known optical power and directing the beam in the direction of a sample;
   B. a detector for measuring optical power in light directed from the direction of the sample; and
   C. a diffuse reflector for redirecting the incoming excitation beam toward the detector from the direction of the sample.

2. The system of claim 1 further including a filter for attenuating a predetermined percentage the light directed by the reflector to the detector.

3. The system of claim 1 wherein the detector includes a plurality of gain settings, and measures optical power at each of the gain settings.

4. The system of claim 3 further including a lookup table that relates the gain settings of the detector to a ratio of the detector power measurements and the known power of the incoming excitation beam.

5. The system of claim 1 wherein the reflector is included on a calibration sample that is positioned in the system for calibration.

6. The system of claim 1 further including a stage for holding the sample, with the reflector positioned on the stage and outside of an associated scanning range, wherein the system scans beyond the scanning range to the reflector during calibration.

7. The system of claim 1 wherein the optical means produces an incoming excitation beam with known variable optical power.

8. The system of claim 7 further including a look-up table that relates the gain settings of the detector to a ratio of the detector power measurements and the known power of the incoming excitation beam.

9. The system of claim 4 further including:
   a. a plurality of filters with known attenuation properties, to attenuate the beam that is redirected by the reflector; and
   b. the lookup table uses the attenuated optical power in the ratio.

10. The system of claim 1 wherein the optical means includes:
    i. a light source for producing the excitation beam;
    ii. a variable optical attenuator for attenuating the excitation beam, to produce the incoming excitation beam,
    iii. directing means for directing the incoming excitation beam in the direction of the sample, and
    iv. a meter for measuring the optical power in the directed incoming excitation beam.

11. The system of claim 10 wherein the meter includes a photodiode that is positioned in the path of the directed incoming excitation beam.

12. The system of claim 11 wherein the directing means includes a lens that focuses the incoming excitation beam to a pixel-sized diameter.

13. The system of claim 1 wherein the optical means focuses the incoming excitation beam to a pixel-sized diameter and the reflector reflects the beam as one or more wide diameter beams.

14. The system of claim 13 wherein the optical means includes a beam splitter that directs wide diameter beams toward the detector and directs narrow diameter beams away from the detector.

15. The system of claim 1 wherein the optical means includes a laser for producing a collimated excitation beam.

16. The system of claim 15 wherein the optical means includes a plurality of lasers and the detector makes measurements associated with the excitation beam produced by each laser.

17. The system of claim 1 wherein the optical means includes a plurality of lasers and the detector makes measurements associated with the light produced by each laser.

18. The system of claim 3 further including
    i. a plurality of lasers in the optical means,
    ii. a plurality of gain settings for the detector, and
    iii. a lookup table that relates the gain settings of the detector to a ratio of detector measurements and the known power of the incoming excitation beam for the wavelengths associated with the respective lasers.

19. A system for calibrating an optical scanner that scans a sample, the system including:
    A. a light source for producing an excitation beam;

B. a variable optical attenuator for attenuating the excitation beam;

C. means for directing the attenuated beam in the direction of the sample; and

D. a meter for measuring the optical power in the attenuated excitation beam at the approximate location where the beam meets a sample during measurement operations.

20. The system of claim 19 wherein the meter measures the optical power at various settings of the attenuator.

21. The system of claim 19 further including a lookup table for relating the attenuator settings to the optical power in the attenuated beam.

22. The system of claim 19 wherein the meter is positioned to receive the attenuated beam when a sample is not in place in the system.

23. The system of claim 22 wherein i. the means for directing the beam focuses the beam to a pixel-sized diameter and ii. the meter includes a photodiode that is positioned in the path of the focused excitation beam.

24. The system of claim 21 further including:

i. a plurality of light sources for producing excitation beams at a plurality of wavelengths, and ii. the lookup table relates the attenuator settings to the optical power in attenuated beams of each wavelength of the plurality of wavelengths.

25. The system of claim 1 further including:

i. a beam splitter for returning to the detector redirected light with predetermined spatial properties and further redirecting away from the detector the redirected light that does not have the predetermined spatial properties; and ii. the diffuse reflector reflecting at least a portion of the incoming excitation beam in a pattern with the predetermined spatial properties.

26. A system for calibrating the sensitivity of an optical scanner, the system including:

A. optical means for producing an incoming excitation beam of known optical power and directing the beam in the direction of a sample, the optical means including a plurality of lasers;

B. a detector for measuring optical power in the attenuated beam directed from the direction of the sample, the detector making measurements associated with the light produced by each laser; and C. a reflector for redirecting the incoming excitation beam toward the detector from the direction of the sample.

27. The system of claim 26 further including:

i. a plurality of gain settings for the detector; and ii. a lookup table that relates the gain setting of the detector to a ratio of the detector measurements and the known power of the incoming excitation beam for the wavelengths associated with the respective lasers.

28. A system for calibrating the sensitivity of an optical scanner, the system including:

A. optical means for producing an incoming excitation beam of known optical power and directing the beam in the direction of a sample, the optical means focusing the incoming excitation beam to a pixel-sized diameter;

B. a detector for measuring optical power in light directed from the direction of the sample;

C. a reflector for redirecting the incoming excitation beam toward the detector from the direction of the sample, the reflector reflecting the beam as one or more wide diameter beams; and D. a beam splitter for directing wide diameter beams toward the detector and narrow diameter beams away from the detector.

29. A system for calibrating the sensitivity of an optical scanner, the system including:

A. optical means for producing an incoming excitation beam of known optical power and directing the beam in the direction of a sample;

B. a reflector for redirecting the incoming excitation beam toward the detector from the direction of the sample;

C. a filter with known attenuation properties for attenuating the redirected excitation beam; and D. a detector for measuring optical power in the attenuated beam directed from the direction of the sample.

* * * * *